United States Patent
Cecchi et al.

(10) Patent No.: US 11,062,216 B2
(45) Date of Patent: Jul. 13, 2021

(54) PREDICTION OF OLFACTORY AND TASTE PERCEPTION THROUGH SEMANTIC ENCODING

(71) Applicant: INTERNATIONAL BUSINESS MACHINES CORPORATION, Armonk, NY (US)

(72) Inventors: Guillermo Cecchi, New York, NY (US); Amit S. Dhurandhar, Yorktown Heights, NY (US); Elkin D. Gutierrez, Jersey City, NJ (US); Pablo Meyer Rojas, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 866 days.

(21) Appl. No.: 15/819,710

(22) Filed: Nov. 21, 2017

(65) Prior Publication Data
US 2019/0156224 A1    May 23, 2019

(51) Int. Cl.
| | |
|---|---|
| *G06N 5/04* | (2006.01) |
| *G06N 20/00* | (2019.01) |
| *G16C 20/70* | (2019.01) |
| *G16C 20/30* | (2019.01) |
| *G16C 20/64* | (2019.01) |

(52) U.S. Cl.
CPC ............... *G06N 5/04* (2013.01); *G06N 20/00* (2019.01); *G16C 20/30* (2019.02); *G16C 20/64* (2019.02); *G16C 20/70* (2019.02)

(58) Field of Classification Search
CPC combination set(s) only.
See application file for complete search history.

(56) References Cited

U.S. PATENT DOCUMENTS

| | | |
|---|---|---|
| 6,523,026 B1 | 2/2003 | Gillis |
| 7,593,863 B1 | 9/2009 | Sunshine et al. |
| 7,827,189 B2 | 11/2010 | Hayama |
| (Continued) | | |

FOREIGN PATENT DOCUMENTS

| | | |
|---|---|---|
| CN | 101603959 A | 12/2009 |
| CN | 102331476 A | 1/2012 |
| (Continued) | | |

OTHER PUBLICATIONS

Edwards et al., "Correlation of odor intensities with structural properties of odorants." Chemical Senses 14.2 (1989): 281-291; 3 pages.

(Continued)

*Primary Examiner* — Michael B Holmes
(74) *Attorney, Agent, or Firm* — Cantor Colburn LLP; Kristofer Haggerty (57) ABSTRACT

Embodiments of the invention include methods, systems, and computer program products for predicting olfactory perception. A non-limiting example of the method includes receiving a library including a plurality of indexed olfactory descriptors. The method also includes receiving an olfactory target descriptor. The method also includes calculating a coefficient matrix and a perceptual distance between an indexed olfactory descriptor and an olfactory target descriptor. The method also includes generating a perceptual descriptor prediction for the olfactory target.

17 Claims, 4 Drawing Sheets

(56) References Cited

U.S. PATENT DOCUMENTS

| | | | |
|---|---|---|---|
| 9,417,221 | B2 | 8/2016 | Varshney et al. |
| 9,519,620 | B1 | 8/2016 | Pinel et al. |
| 9,595,006 | B2 * | 3/2017 | Dhurandhar .............. G06N 5/04 |
| 9,600,773 | B2 * | 3/2017 | Dhurandhar ............ G08B 21/18 |
| 9,665,828 | B2 | 5/2017 | Pinel et al. |
| 9,721,008 | B1 | 8/2017 | Byron et al. |
| 9,775,339 | B1 * | 10/2017 | Gifford ................... H01L 21/31 |
| 9,915,942 | B2 * | 3/2018 | Baseman ......... G05B 19/41875 |
| 10,028,609 | B2 | 7/2018 | Snyder |
| 10,251,390 | B2 * | 4/2019 | Gifford ................... A01N 25/34 |
| 10,349,653 | B2 * | 7/2019 | Gifford ................... B82Y 30/00 |
| 10,395,300 | B2 * | 8/2019 | Chong ............... G06K 9/00268 |
| 10,467,631 | B2 * | 11/2019 | Dhurandhar ......... G06Q 20/102 |
| 10,656,158 | B2 * | 5/2020 | Rojas .................... G01N 33/573 |
| 10,665,330 | B2 * | 5/2020 | Cecchi .................... G16C 20/30 |
| 10,740,860 | B2 * | 8/2020 | Baldini Soares ....... G06F 16/35 |
| 10,776,855 | B2 * | 9/2020 | Dhurandhar ....... G06Q 30/0631 |
| 10,832,308 | B2 * | 11/2020 | Dhurandhar ....... G06Q 30/0631 |
| 2005/0096852 | A1 | 5/2005 | Turin |
| 2008/0114564 | A1 * | 5/2008 | Ihara ..................... G06K 9/6215 702/158 |
| 2010/0143337 | A1 | 6/2010 | Matsunami |
| 2010/0248390 | A1 | 9/2010 | Matsunami |
| 2012/0015841 | A1 | 1/2012 | Shekdar |
| 2012/0143804 | A1 | 6/2012 | Haddad et al. |
| 2013/0270400 | A1 | 10/2013 | Bartoshuk |
| 2014/0245350 | A1 * | 8/2014 | Goel ........................ G06T 5/005 725/34 |
| 2015/0235136 | A1 | 6/2015 | Dillon |
| 2015/0223458 | A1 | 8/2015 | Ray |
| 2015/0300945 | A1 * | 10/2015 | Gao ..................... G01N 21/274 702/104 |
| 2016/0091419 | A1 | 3/2016 | Watson et al. |
| 2018/0089739 | A1 | 3/2018 | Cecchi |
| 2019/0171673 | A1 * | 6/2019 | Sobel ................... A61B 5/4011 |
| 2019/0254322 | A1 | 8/2019 | Bartoshuk et al. |
| 2019/0338226 | A1 * | 11/2019 | Agos N Trumper ..... C12F 3/04 |
| 2019/0380657 | A1 * | 12/2019 | Pereira ................... A61B 34/10 |

FOREIGN PATENT DOCUMENTS

| | | | |
|---|---|---|---|
| WO | 2005078433 | A1 | 8/2005 |
| WO | 2013035070 | A1 | 3/2013 |
| WO | 2015037003 | A1 | 3/2015 |

OTHER PUBLICATIONS

Kerman et al., "Molecular complexity determines the number of olfactory notes and the pleasantness of smells." Scientific reports 1 (2011): 206; 19 pages.

Khan, et al. "Predicting Odor Pleasantness from Odorant Structure: Pleasantness as a Reflection of the Physical World," The Journal of Neuroscience, Sep. 12, 2017, No. 27(37):10015-10023; 9 pages.

Lawless et al., "Consistency of multidimensional scaling models derived from odor sorting." Journal of Sensory Studies 5.4 (1990): 217-230; 3 pages.

Mateo, "Recognition systems and biological organization: the perception component of social recognition," Annales Zoologici Fennici. Finnish Zoological and Botanical Publishing Board, 2004: pp. 729-745.

Snitz, et al. "Predicting Odor Perceptual Similarity from Odor Struture," PLOS Computational Biology, Sep. 2013, vol. 9, issue 9, e1003184; pp. 1-12.

Yan, et al. "Use of a Modified Vector Model for Odor Intensity Prediction of Odorant Mixtures," Sensors 2015, 15, pp. 5697-5709; doi: 10.3390/s150305697, 13 pages.

Zarzo, "Hedonic judgments of chemical compounds are correlated with molecular size." Sensors 11.4 (2011): pp. 3667-3686. http://www.mdpi.com/1424-8220/111413667/htm.

Keller, et al. "Personalized predictions of human odour perceptual attributes from chemical features," Published Date: Unknown; 32 pages.

Y-Y. Ahn et al., "Flavor network and the principles of food pairing," Nature, Scientific Reports, vol. 1, No. 196, 2011, 7 pages.

A. Keller et al., "Reverse-engineering human olfactory perception from chemical features of odor molecules," bioRxiv, Posted Oct. 21, 2016, 082495.

Guillermo A. Cecchi et al. "Correlating Olfactory Perception With Molecular Structure", U.S. Appl. No. 15/296,597, filed Oct. 18, 2016.

List of IBM Patents or Patent Applications Treated as Related; (Appendix P), Filed Nov. 21, 2017.

Baldwin, Elizabeth A. et al., "Electronic Noses and Tongues: Applications for the Food and Pharmaceutical Industries USDA-ARS Citrus & Subtropical Products Laboratory," 600 Ave S N.W., Winter Haven, FL 33881, USA Published: May 2, 2011.

Buratti, D. et al., "Prediction of Italian red wine sensorial descriptors from electronic nose, electronic tongue and spectrophotometric measurements by means of Genetic Algorithm regression models," Original Research Article Food Chemistry, vol. 100, Issue 1, 2007, pp. 211-218S.

Ricci, Francesco et al., "Introduction to Recommender Systems Handbook," Recommender Systems Handbook, Springer, 2011, pp. 1-35.

Rodgers, Sarah et al., "Characterizing Bitterness: Identification of Key Structural Features and Development of a Classification Model" J. Chem. Inf. Model., 2006,46 (2), pp. 569-576DOI: 10.1021/ci0504418.

Szllosi, SweeDniel et al., "Recognition and Taste Prediction of Coke Drinks by Electronic Tongue," IEEE Sensors Journal, vol. 12, No. 11, Nov. 2012.

* cited by examiner

PREDICTION OF OLFACTORY AND TASTE PERCEPTION THROUGH SEMANTIC ENCODING

BACKGROUND

The present invention generally relates to olfactory perception, and more specifically, to prediction of olfactory and taste perception through semantic encoding.

Molecular compounds and mixtures of molecular compounds can exhibit various olfactory and taste characteristics that elicit a variety of human responses including a variety of linguistic characterizations. Speech analysis and characterization of taste and smell can be conveyed in words, sentences, paragraphs, facial expressions, and even books. Recent studies have suggested that humans have a relatively high capability of discriminating between various odors, theoretically being able to distinguish between trillions of mixtures. On the other hand, the ability to recognize or characterize odors by description can be relatively more limited. For instance in some cases only a handful of descriptors are available to distinguish between a larger set of distinguishable odors or tastes. Moreover chosen descriptors for a taste or smell can vary from person to person.

SUMMARY

Embodiments of the present invention are directed to a computer-implemented method for predicting olfactory perception. A non-limiting example of the computer-implemented method includes receiving, by a processor, a library including a plurality of indexed olfactory descriptors. The method also includes receiving, by the processor, an olfactory target descriptor. The method also includes calculating, by the processor, a coefficient matrix and a perceptual distance between an indexed olfactory descriptor and an olfactory target descriptor. The method also includes generating a perceptual descriptor prediction for the olfactory target.

Embodiments of the invention are directed to a computer program product for predicting olfactory perception, the computer program product including a computer readable storage medium having program instructions embodied therewith. The program instructions are executable by a processor to cause the processor to perform a method. A non-limiting example of the method includes receiving, by a processor, a library including a plurality of indexed olfactory descriptors. The method also includes receiving, by the processor, an olfactory target descriptor. The method also includes calculating, by the processor, a coefficient matrix and a perceptual distance between an indexed olfactory descriptor and an olfactory target descriptor. The method also includes generating a perceptual descriptor prediction for the olfactory target.

Embodiments of the present invention are directed to processing system for predicting olfactory perception. The system includes a processor in communication with one or more types of memory, the processor configured to perform a method. A non-limiting example of the method includes receiving a library including a plurality of indexed olfactory descriptors. The method also includes receiving an olfactory target descriptor. The method also includes calculating a coefficient matrix and a perceptual distance between an indexed olfactory descriptor and an olfactory target descriptor. The method also includes generating a perceptual descriptor prediction for the olfactory target.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, humans share with other species the ability to make subtle discriminative judgments of sensory information and act accordingly. For example, the olfactory pathway includes around 400 different receptors, allowing for a high dimensionality or complexity of sensory input.

Unique to humans, olfactory-based judgments can be made with expressions of language. Cross-modal effects have been reported with respect to odor perception. For instance, the primary olfactory cortex can be activated during passive reading of odor related words. For instance, an odor can be characterized as sweet, woody, sour, or spicy. However, although potentially trillions of mixtures can have distinct or identifiable odors, a similarly expansive universal system of characterizing or recognizing such odors by name does not exist. In addition, individualized expressions of olfactory signals can vary from person to person and can depend on a wide variety of factors, including the type of odor or taste, the complexity of the odor or taste, the language capacity of the individual communicating the olfactory perception, or even the context of the individual. For instance, a wine connoisseur or sommelier could be expected to recite a vastly different description of a particular wine, including identification for instance of particular fruits, nuts or butter in the taste of a particular sample, than a casual wine drinker who could simply describe a sample as sweet or pleasant.

Prediction and characterization of olfactory perception remains challenging. For instance, some conventional methods rely upon controlled rating systems of smell or taste tests, which can require the sampling of several individuals for characterization of a single smell or taste. In some cases, molecular structure information can be leveraged to predict certain olfactory semantic descriptors. However, such methods can require the a priori characterization of a chemical feature of a substance and the resultant characterization can be limited to those characterizations provided in a controlled setting. Systems and methods to broadly characterize and predict olfactory perception, without cumbersome testing, are needed.

Turning now to an overview of the aspects of the invention, one or more embodiments of the invention address the above-described shortcomings of the prior art by providing a prediction of olfactory perception characteristics of an object using semantic descriptors. Embodiments of the invention can provide expansive and detailed descriptions of olfactory perceptions and can leverage natural language descriptions to generalize and/or translate a description without the need for controlled testing. Embodiments of the invention provide a predictive olfactory perception profile of a substance or object based at least in part upon descriptors and olfactory perception profiles of other substances or objects.

The above-described aspects of the invention address the shortcomings of the prior art by generating a relationship between a perceptual descriptor of an olfactory sense (i.e., taste or smell) of a first olfactory library or set of descriptors and a second set of descriptors including human language. Using this relationship information along with perceptual ratings from other models, such as chemoinformatic models, a predictive semantic description of a larger dimension can be generated. In some embodiments of the invention, olfactory sense analysis using language (including words, sentences, paragraphs, and the like) and facial expressions are applied to systematize and quantify knowledge with respect to perceptual descriptions of taste and odors. In some embodiments of the invention, natural narrative descriptions of desired perceptual targets, also referred to herein as semantic descriptors, can be used to identify corresponding matching single molecules or mixtures through reverse engineering.

In some embodiments of the invention, semantic descriptors can complement or supplement perceptual descriptors generated based upon molecular structures to generate an olfactory perception prediction for an object. For example, where a chemoinformatic model based solely upon molecular structure generates a rating prediction of specific olfactory semantic descriptors, speech analytics including, for instance, natural language processing (NLP) can expand the initial rating prediction to provide more detailed semantic descriptors, for instance expanding an initial rating for flower to infer and/or predict ratings for specific types of flowers, including rose, freesia, lily, daisy, and marigold. Some embodiments of the invention provide whole sentence descriptors of an odor or taste sensation to provide a ranked match of comparable or equivalent molecules or mixtures.

Embodiments of the invention can enable prediction and characterization of attributes of objects and substances based upon the taste and/or smell of other objects and substances without laboratory controlled settings.

Figure 1:
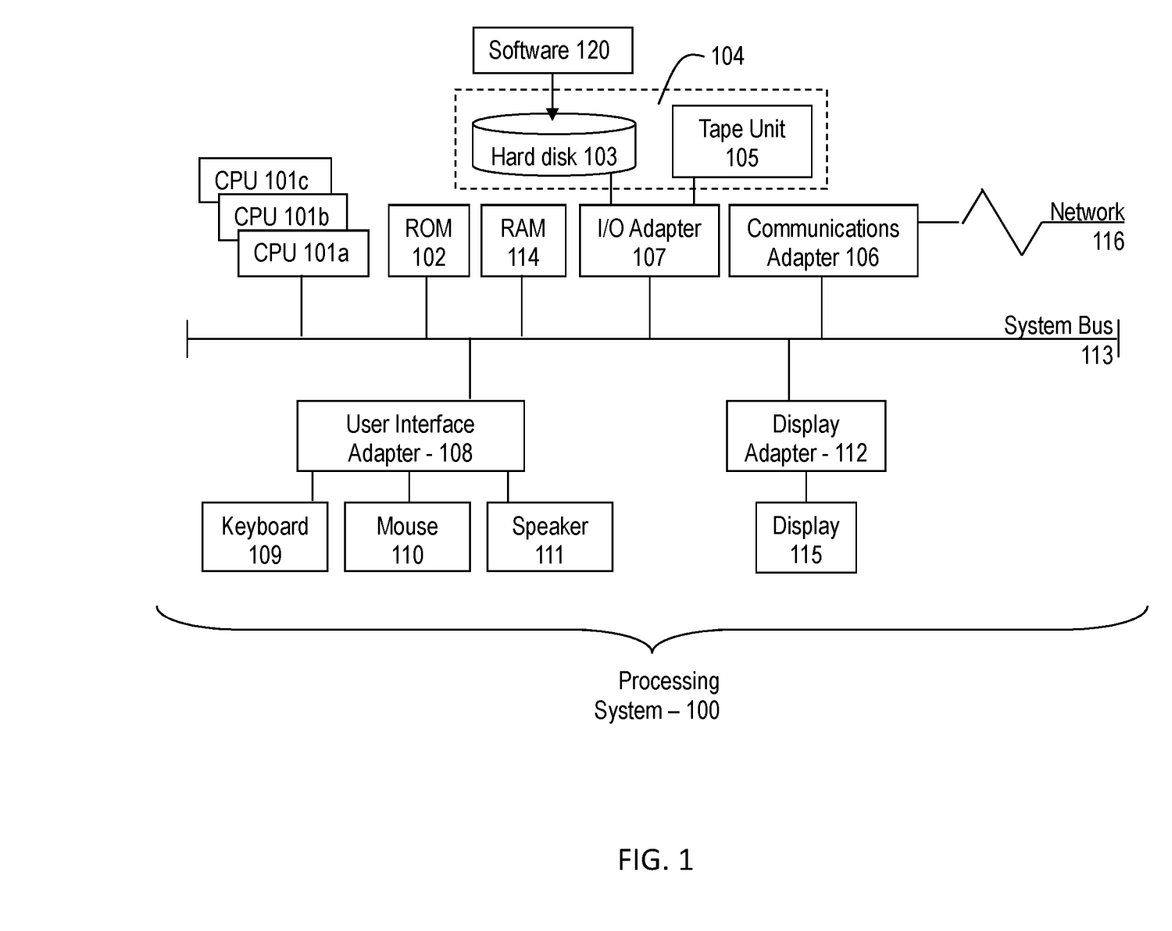
FIG. 1 is block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104.

Software 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
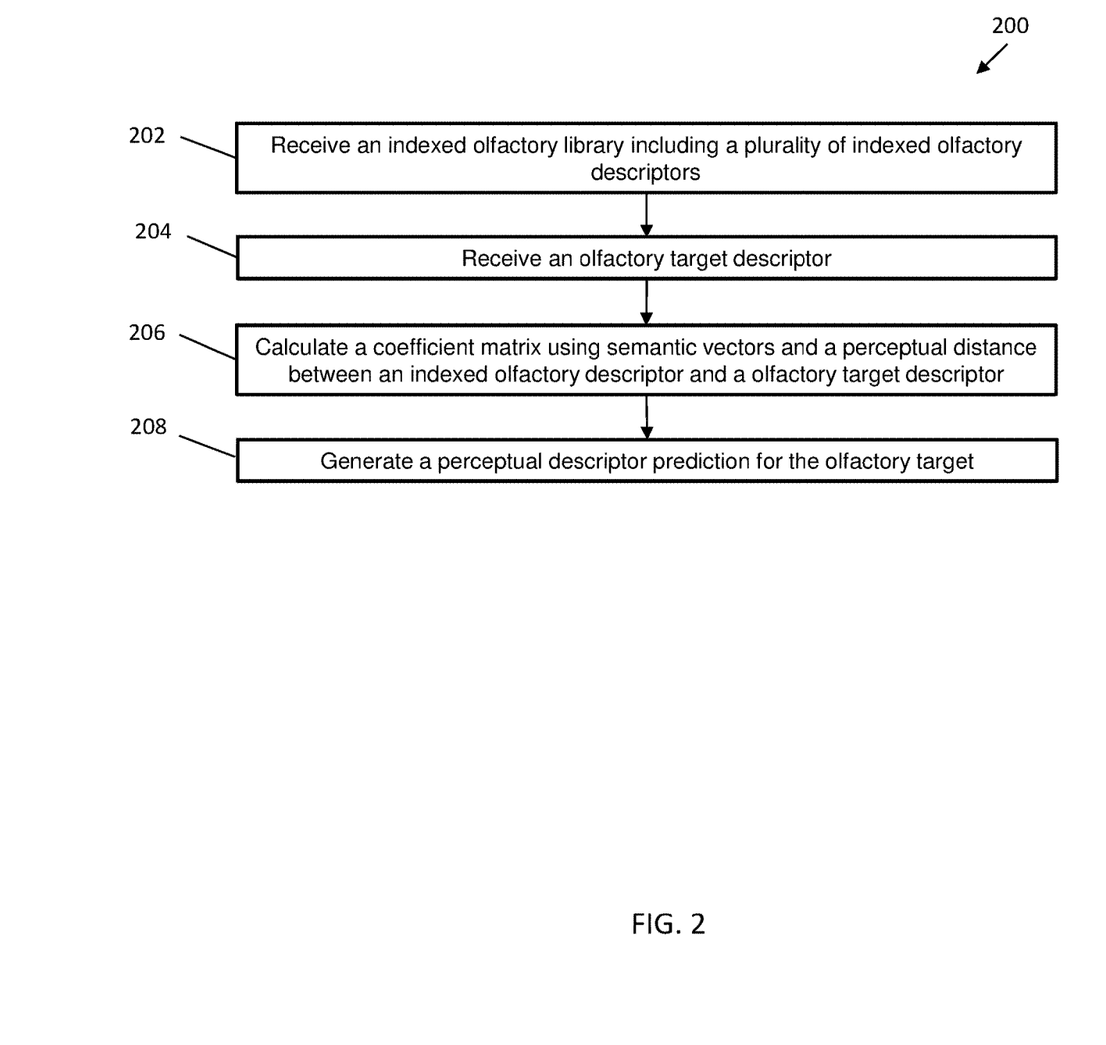
FIG. 2 depicts a flow diagram illustrating a method according to one or more embodiments of the invention.

Turning now to a more detailed description of aspects of the present invention, FIG. 2 depicts a flow diagram of an exemplary method 200 according to embodiments of the invention. The method 200 includes, as shown at block 202, receiving an indexed olfactory library including a plurality of indexed olfactory descriptors.

Olfactory perceptions include quantitative and qualitative taste or smell perceptions. Olfactory descriptors can include numerical, verbal, or visual descriptors of olfactory perceptions. In some embodiments of the invention, olfactory descriptors include molecular descriptors, semantic descriptors, or combinations including molecular descriptors and semantic descriptors. In some embodiments of the invention, olfactory descriptors include only semantic descriptors. In some embodiments of the invention, olfactory descriptors include semantic descriptors and molecular descriptors.

Semantic descriptors can include any linguistic, visual, and auditory characterizations of the taste or smell of a substance or object. Semantic descriptors can include, for example, words, sentences, paragraphs, books, treatises, facial expressions, drawings, or music that describe a taste or smell. Semantic descriptors can be general, such as "pleasant" "spicy," or object-specific, such as "garlic." Semantic descriptors can be included in semantic vectors, which are vectorial representations of word meaning motivated by the distributional hypothesis. Semantic vectors can be generated by known methods, such as the Word2Vec continuous-bag-of-words algorithm.

In some embodiments of the invention, semantic vectors include a source set of perceptual descriptors, which includes one or more sets of perceptual descriptors associated with a plurality of chemicals or objects. In some embodiments of the invention, the source set of perceptual descriptors can be derived from a model trained to infer the ratings scores of a chemical based upon a limited source set of perceptual descriptors, such as the model trained by Keller et al., *Frontiers in systems neuroscience*, eaal 2014, 2017. For a number of source set of perceptual descriptors $D_S$ the source-set ratings scores for each chemical i can be collected into a perceptual vectors $p_{S,i}$ of length $V_S$. For each descriptor d in the source set, a semantic vector $s_{S,d}$ can be computed.

In some embodiments of the invention, the source set of perceptual descriptors can be derived from direct measurement. For example, perceptual vectors $p_{S,i}$ can be generated from data obtained by direct measurement, such as by obtaining perceptual data, such as ratings or semantic descriptions, from human subjects.

Molecular descriptors can include chemical information, such as chemical formulas, structures, substructures, and physical properties. Molecular descriptors can be included in chemoinformatic feature vectors that summarize the chemical and/or molecular properties of a substance.

Molecular descriptors can include 0D-descriptors, 1D-descriptors, 2D-descriptors, 3D-descriptors, and 4-D descriptors. 0D-descriptors can include, for example, constitutional descriptors that describe the arrangement of elements within a molecule, the types of chemical bonds present in the molecule, etc. 0D-descriptors can further include count descriptors that indicate, for example, the number of atoms of each element present in a molecular compound. 1D-descriptors can include, for example, lists of structural fragments, fingerprints, or the like. 2D-descriptors can include, for example, graph invariants or the like. 3D-descriptors can include, for example, 3D-Molecule Representation of Structure based on Electron Diffraction (MoRSE) descriptors; Weighted Holistic Invariant Molecular (WHIM) descriptors; Geometry, Topology, and Atom Weights Assembly (GETAWAY) descriptors; quantum-chemical descriptors; size, steric, surface, and volume descriptors; or the like. 4D-descriptors can include, for example, Grid-Independent descriptors (GRIND) or descriptors obtained through Comparative Molecular Field Analysis (CoMFA) methods. The set of molecular descriptors that is used can include any combination of the above-described types of molecular descriptors. Further, in certain example embodiments, a descriptor must satisfy various criteria in order to be used. For example, a molecular descriptor can need to be invariant to molecular numbering or labeling.

Indexed olfactory descriptors include olfactory descriptors associated with a substance, object, or with other olfactory descriptors. Olfactory target descriptors include a descriptor of a substance or object that is sought to be described further or in a different manner.

The method 200 includes, as shown at block 204, receiving an olfactory target descriptor. As used herein, an "olfactory target" is understood to mean an object, substance, or descriptor for which a perceptual olfactory description is desired. An olfactory target descriptor can include, for example, new substances or objects that have no predetermined perceptual descriptor, substances or objects that have a perceptual descriptor but for which a new or additional set of perceptual descriptors are sought, and/or a perceptual descriptors, such as description of taste or smell, for which a set of related descriptions are desired.

The method 200 includes, as shown at block 206, calculating a coefficient matrix using semantic vectors and a perceptual distance between an indexed olfactory descriptor and an olfactory target descriptor. The method 200 also includes, as shown at block 208, generating a perceptual descriptor prediction for the olfactory target.

A coefficient matrix and perceptual distances can be calculated by known techniques. For example, a coefficient matrix for computing vector distances, including for instance regression models such as LASSO and elastic net regression. LASSO and elastic net, for example, can impose a regularization penalty on regression weights to reduce model complexity and avoid overfitting.

For example, for each descriptor d in a source set, semantic vector $s_{S,d}$ is generated as a 300-dimensional vector generated by a regression technique. These can be collected into a source semantic matrix $S_S$ of dimension $D_S \times 300$ where $D_S$ is the number of perceptual descriptors (such as source-set rating scores). To determine ratings scores for any set of perceptual descriptors, such as perceptual descriptors for an olfactory target, it is assumed that semantic descriptors corresponding to each perceptual descriptor d can be computed, and these are collected into a target semantic matrix ST of dimension DT×300, wherein DT is the number of target perceptual descriptors, including semantic descriptors for the olfactory target. Rating scores for each target molecule or substance i, for example, can then be estimated through a model. In some embodiments of the invention, the model is a semantics-only model.

A semantics model leverages the structure of the semantic space to predict ratings in the perceptual ratings space. For instance, it can be supposed there exists a coefficient matrix or function F of dimension $D_S \times D_T$ that roughly maps from the semantic vectors for the source set of perceptual descriptors to the semantic vectors for a target set of perceptual descriptors, such that $$S_T \approx \Gamma S_S.$$

A semantics-only model assumes that $\Gamma$ maps from the perceptual ratings for the source set of descriptors to the perceptual ratings for the target set for each molecule or substance i:

$$p^{T,i} \approx \Gamma p_{S,i}.$$

Elastic net regression can be used, for example, to estimate $\Gamma$. Such model, for example, does not require a rating score for the source set. Where target descriptor training molecules are available, an estimate for molecule or substance i can be:

$$p^{T,i} \approx \Gamma p_{S,i} + \bar{p}_T.$$

In some embodiments of the invention, the model is a combined semantics and ratings model. In such embodiments of the invention, the predictions of semantics-only models can be averaged with predictions of ratings-only models. Ratings-only models can be generated, for example by assuming a function $\Lambda$ that maps from ratings scores on source descriptors to rating scores on target descriptors for a training set of molecules or substances. Mean ratings can be included, for example, and a final estimate can be $$p^{T,i} \approx \Lambda p_{S,i} + \bar{p}_T.$$

Figure 3:
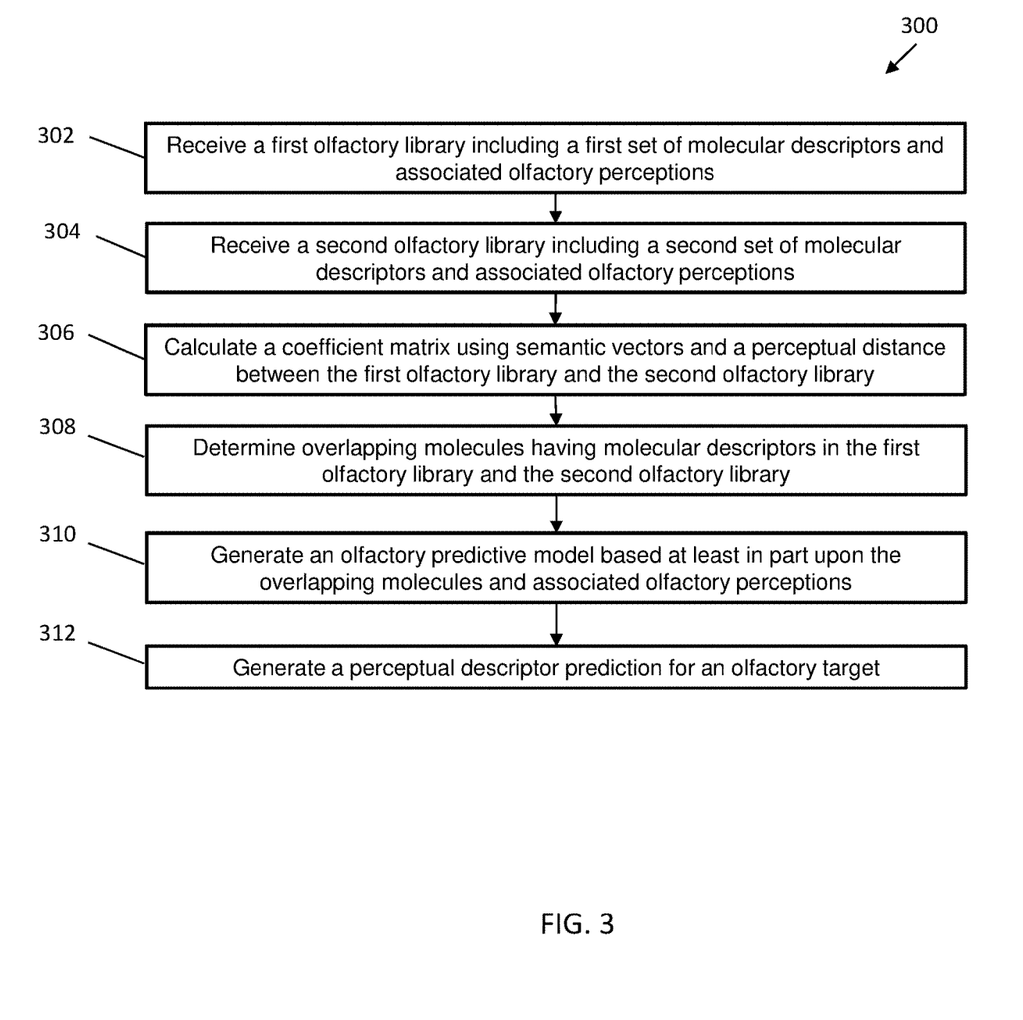
FIG. 3 depicts a flow diagram illustrating a method according to one or more embodiments of the invention.

FIG. 3 depicts a flow diagram of another exemplary method 300 according to embodiments of the invention. The method 300 includes, as shown at block 302 receiving a first olfactory library including a first set of molecular descriptors and associated olfactory perceptions. For instance, the first olfactory library can include a low complexity library including a small set, such as 20 or 21, of perceptual semantic descriptors indexed to a number of molecules.

The method 300 includes, as shown at block 304, receiving a second olfactory library including a second set of molecular descriptors and associated olfactory perceptions. For example, second olfactory library can include a dataset can be received from individuals that smelled a small library of molecules including a complex description of the individuals' olfactory perception using a set of refined words, sentences, drawings, facial expressions, numerical ratings or rankings, and the like. A second olfactory library can include an identification of molecules or substances, such as molecules that overlap with the first olfactory library.

The first and second olfactory libraries can have perceptual descriptors with the same or different complexities. For instance, a first olfactory library can have low complexity descriptors, for instance descriptors consisting of single words or short phrases, and the second olfactory can have high complexity descriptors, including a set of refined words, sentences or longer language expressions, drawings, or facial expressions. The first and second olfactory libraries can have the same or different sized data sets.

The first olfactory library, in some embodiments of the invention, is a known library including a set of molecular descriptors and associated olfactory perceptions, such as the Dravnieks dataset including 126 molecules represented by molecular descriptors and 146 words as associated olfactory perceptions (citrus, lemon, grapefruit, orange, fruity, other than citrus, stale, coffee, tobacco, smoke, . . . ), and/or the DREAM dataset of 470 molecules represented by molecular descriptors and 21 words as associated olfactory perceptions.

In some embodiments of the invention, associated olfactory perceptions are generated with natural language processing. In some embodiments of the invention, associated olfactory perceptions include refined semantic descriptors. Refined semantic descriptors is understood to mean descriptors that have a higher level of complexity than a limited set of single word descriptors in an olfactory library, wherein the number of single word descriptors in some embodiments of the invention in the olfactory library is less than 100, or less than 50.

The method 300 includes, as shown at block 306, calculating a coefficient matrix and a perceptual distance between the first olfactory library and the second olfactory library. The method 300 includes, as shown at block 308, determining overlapping molecules having molecular descriptors in the first olfactory library and the second olfactory library. For example, and overlapping molecule can be described by a molecular descriptor, such as "methane," in the first and second olfactory libraries. In some embodiments of the invention, the first and second olfactory libraries share overlapping molecular descriptors, such as at least 20% overlap or at least 25% overlap of molecular descriptors based upon the total number of molecular descriptors in the libraries. The overlapping molecular descriptors can have the same or different associated olfactory perceptions in the first and second olfactory libraries. For example, "$NH_4$" can have an associated olfactory perception of "ammonia" in the first olfactory library and "strong pungent urine-like smell that induces eyes to water and sometimes makes it difficult to breathe" perception in the second olfactory library.

The method 300 includes, as shown at block 310, generating an olfactory predictive model based at least in part upon the overlapping molecules and associated olfactory perceptions. In some embodiments of the invention, the predictive model is based at least in part upon natural language processing. The method 300 includes, as shown at block 312, generating a perceptual descriptor prediction for an olfactory target. The perceptual descriptor prediction can include a set of refined descriptors for one or more olfactory targets.

Molecular descriptors include common or scientific names, chemical formula, or other representative descriptions of a molecule or substance. As used herein, unless otherwise stated, molecular descriptors are not limited to units of one molecule and can include chemical sub-structures, chemical compositions including a plurality of molecules, and/or substances or objects including such molecules and compositions.

Figure 4:
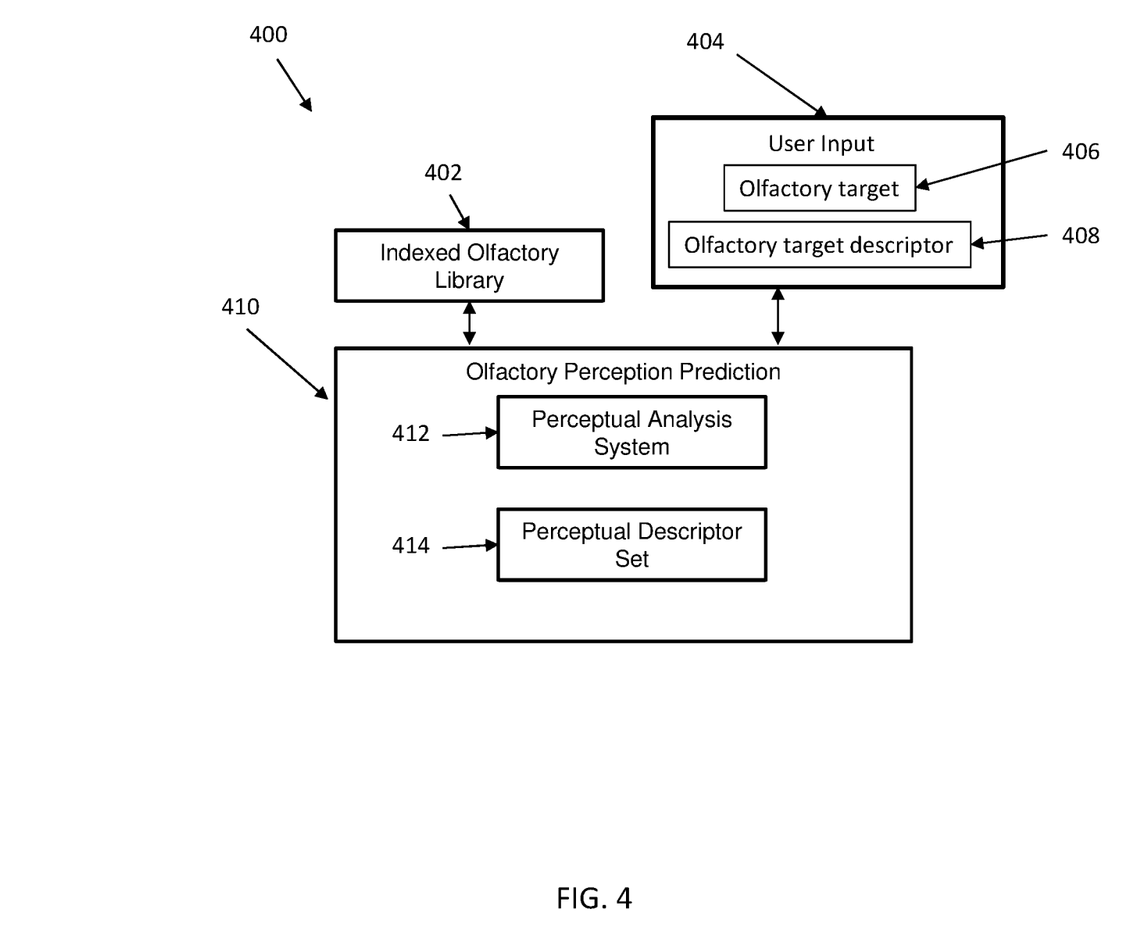
FIG. 4 is a schematic of a system according to one or more embodiments of the invention.

FIG. 4 depicts a block diagram of an exemplary system 400 according to embodiments of the invention. The system 400 can include an indexed olfactory library 402 in communication with an olfactory perception prediction engine 410. The Olfactory perception prediction engine 410 can be in communication with a user input 404 including an olfactory target 406 and/or an olfactory target descriptor 408. The Olfactory perception prediction engine includes a perceptual analysis system 412 and a perceptual descriptor set 414. The perceptual analysis system 412 can include speech analysis, such as natural language processing systems. The perceptual descriptor set 414 can include predicted perceptual descriptors for one or more targets and can be generated based at least in part upon a predictive model based upon overlapping molecules or substances.

Example embodiments of the invention provide various technical features, technical effects, and/or improvements to technology. For instance, example embodiments of the invention provide the technical effect of predicting olfactory perception for a single individual or across a group of individuals based open ended semantic descriptors. This technical effect is achieved by at least in part by the technical feature of calculating a coefficient matrix and perceptual distances between perceptual semantic descriptors. Example embodiments of the invention also provide the technical effect of transforming an olfactory or taste perception from one space of perceptual descriptors to a more Example embodiments of the invention also provide the technical effect of generating a substance or object having desired olfactory properties. This technical effect is achieved at least in part by the technical feature of predicting a perceptual descriptor set for a target substance or object. The above-described technical effects constitute an improvement to the functioning of a computer configured to predict olfactory perception of chemical compounds and mixtures. In addition, the above-described technical effects constitute an improvement to any of a variety of technological fields including any of those previously described such as, for example, appetite management, odor cancellation, or the like. It should be appreciated that the above examples of technical features, technical effects, improvements to the functioning of a computer, and improvements to technological fields provided by example embodiments of the invention are merely illustrative and not exhaustive.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application or technical improvement over technologies found in the marketplace, or to enable others of ordinary skill in the art to understand the embodiments described herein.

What is claimed is:

1. A computer-implemented method for predicting olfactory perception, the method comprising:
    receiving, by a processor, a library including a plurality of indexed olfactory descriptors, wherein the indexed olfactory descriptors comprise molecular descriptors and semantic descriptors;
    receiving, by the processor, an olfactory target descriptor;
    calculating, by the processor, a coefficient matrix and a perceptual distance between an indexed olfactory descriptor and an olfactory target descriptor; and
    generating a perceptual descriptor prediction for the olfactory target.

2. The computer-implemented method of claim 1, wherein the library comprises chemoinformatic vectors.

3. The computer-implemented method of claim 1, wherein the library comprises semantic vectors.

4. The computer-implemented method of claim 1 further comprising generating a source semantic matrix based at least in part upon a plurality of source semantic vectors and generating a target semantic matrix based at least in part upon a plurality of target semantic vectors.

5. The computer-implemented method of claim 1, wherein the coefficient matrix is calculated by regression.

6. The computer-implemented method of claim 1, wherein the indexed olfactory library comprises a set of molecular descriptors and associated olfactory perceptions.

7. A computer program product for predicting olfactory perception, the computer program product comprising:
    a non-transitory computer readable storage medium readable by a processing circuit and storing program instructions for execution by the processing circuit for performing a method comprising:
    receiving a library including a plurality of indexed olfactory descriptors, wherein the library comprises chemoinformatic vectors;
    receiving an olfactory target descriptor;
    calculating a coefficient matrix and a perceptual distance between an indexed olfactory descriptor and an olfactory target descriptor; and
    generating a perceptual descriptor prediction for the olfactory target.

8. The computer program product of claim 7, wherein the indexed olfactory descriptors comprise molecular descriptors and semantic descriptors.

9. The computer program product of claim 7, wherein the library comprises semantic vectors.

10. The computer program product of claim 7, wherein the method further comprises generating a source semantic matrix based at least in part upon a plurality of source semantic vectors and generating a target semantic matrix based at least in part upon a plurality of target semantic vectors.

11. The computer program product of claim 7, wherein the coefficient matrix is calculated by regression.

12. The computer program product of claim 7, wherein the indexed olfactory library comprises a set of molecular descriptors and associated olfactory perceptions.

13. A processing system for predicting olfactory perception, the system comprising:
    a processor in communication with one or more types of memory, the processor configured to perform a method comprising:
    receiving a library including a plurality of indexed olfactory descriptors;
    receiving an olfactory target descriptor;
    generating a source semantic matrix comprising a first dimension (Ds) based at least in part upon a plurality of source semantic vectors;
    generating a target semantic matrix comprising a second dimension (Dt) based at least in part upon a plurality of target semantic vectors;
    calculating a coefficient matrix of dimension Ds×Dt and a perceptual distance between an indexed olfactory descriptor and an olfactory target descriptor; and
    generating a perceptual descriptor prediction for the olfactory target.

14. The processing system of claim 13, wherein the indexed olfactory descriptors comprise molecular descriptors and semantic descriptors.

15. The processing system of claim 13, wherein the library comprises chemoinformatic vectors.

16. The processing system of claim 13, wherein the library comprises semantic vectors.

17. The processing system of claim 13, wherein the coefficient matrix is calculated by regression.

* * * * *